(12) United States Patent
Szego

(10) Patent No.: US 6,727,347 B1
(45) Date of Patent: Apr. 27, 2004

(54) METHOD FOR PREPARING POLYCATION BASED BIOCONJUGATES SUITABLE FOR TRANSPORTING DIFFERENT KINDS OF ACTIVE SUBSTANCES WITHIN THE BODY

(76) Inventor: Peter Szego, Istenhegyi ut 88, Budapest H-1125 (HU)

( * ) Notice: Subject to any disclaimer, the term of this patent is extended or adjusted under 35 U.S.C. 154(b) by 8 days.

(21) Appl. No.: 10/018,806

(22) PCT Filed: Jun. 28, 2000

(86) PCT No.: PCT/HU00/00061

§ 371 (c)(1),
(2), (4) Date: May 7, 2002

(87) PCT Pub. No.: WO01/00242

PCT Pub. Date: Jan. 4, 2001

(30) Foreign Application Priority Data

Jun. 29, 1999 (HU) .............................. 9902217

(51) Int. Cl.⁷ .......................... A61K 47/48; C07K 14/00
(52) U.S. Cl. .................. 530/345; 424/9.34; 424/178.1; 514/2; 514/44; 530/300; 530/350; 530/391.1; 530/402; 530/409; 530/410; 536/23.1
(58) Field of Search ................................. 424/9.3, 9.34, 424/9.341, 178.1; 514/2, 44; 580/300, 345, 350, 402, 408, 409, 410; 534/10, 11, 12, 14, 15; 536/23.1; 530/391.1

(56) References Cited

U.S. PATENT DOCUMENTS

| | | | |
|---|---|---|---|
| 4,701,521 A | 10/1987 | Ryser et al. | 530/322 |
| 4,847,240 A | 7/1989 | Ryser et al. | 514/12 |
| 5,849,893 A | * 12/1998 | Lobberding et al. | 536/23.1 |

FOREIGN PATENT DOCUMENTS

| | | |
|---|---|---|
| DE | 38 35 962 A-2 | 6/1989 |
| GB | 2212 810 A | 8/1989 |

OTHER PUBLICATIONS

Shima et al. Polylysine Produced by Streptomyces. AGric. Biol. Chem. 1977, vol. 41, No. 9, pp. 1807–1809.*

Shima et al. Binding of Metal Ions by alpha–Poly–L–Lysine and epsilon–Poly–L–Lysine. Journal of Polymer Science: Polymer Letters Edition. 1985, vol. 23, pp. 245–249.*

Inaki et al. Isopoly–L–Ornithine Derivatives Of Thymine and Thymidine. Nucleosides & Nucleotides. 1998. vol. 17, Nos. 1–3, pp. 339–350.*

Kricheldorf et al. Binding of Nucleosides to Basic Polypeptides via Isocyanato–isothiocyanates. Die Makromolekulare Chemie. 1980, vol. 181, pp. 2571–2585.*

Nosho et al. Synthesis And Antimicrobial Activity of N–alpha–Poly–Acyl–N–Epsilon–Poly–L–Lysine Derivatives. Chemistry Express. 1992, vol. 7, No. 10, pp. 753–756.*

Ho et al. Improving Emulsifying activity of epsilon–polylysine by conjugation with dextran through the Maillard reaction. Food Chemistry. 2000, vol. 68, pp. 449–455.*

Uchegbu, I.F. et al., "Polymeric vesicles from amino acid homopolymers," Proc. Int. Symp. Controlled Release Bioact. Mater., 25: 186–187 (1998).

Wang, W. et al., "Polymeric vesicle prepared from poly–L–lysine modified amphiphilic graft copolymer," Proc. Int. Symp. Controlled Release Bioact. Mater. 27: 367–368 (2000).

Seidenberger, H. et al., "Untersuchungen uber die Zusammenhange zwischen Struktur und Antitumorwirkung bei cis–Dichlorobis(oligopeptidester)platin–(II)–Komplexen," Arch. Pharm. (Weinheim)316(2):121–131 (1983)—English abstract enclosed.

* cited by examiner

Primary Examiner—Jeffrey E. Russel
(74) Attorney, Agent, or Firm—Andrea G. Reister; Covington & Burling

(57) ABSTRACT

Polycation bioconjugates and a method for producing them. The polycations are capable of transporting active substances of different types. The polycations function as carrier molecules that transport enhancer molecules, thereby enhancing the biological effectiveness of the transported molecules. The polycation bioconjugates of the present invention may inhibit malignant cell proliferation, possess antimicrobial effect, or be configured for gene transport.

20 Claims, No Drawings

METHOD FOR PREPARING POLYCATION BASED BIOCONJUGATES SUITABLE FOR TRANSPORTING DIFFERENT KINDS OF ACTIVE SUBSTANCES WITHIN THE BODY

Subject of the present invention is the preparation of polycation based bioconjugates that are suitable for transporting active substances of different type within the body, that is for functioning as carriers.

New polycation bioconjugates according to the invention are prepared by coupling [(k)Mx] and/or [(i)Mx] molecules, bearing functional groups appropriate for conjugation—which may either be identical ones or of (two or more i.e. "x") different kind—to a given representative of isopolypeptide polycations, having free α-amino groups, as carrier molecules, by chemical bonds; and the bioconjugates synthetized this way can be described by the general formula (I):

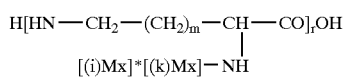

and within the polycation bioconjugatis there are isopolypeptide polycation carrier molecules (further on: carrier molecules), having free α-amino groups, that can be described by the general formula (I/a):

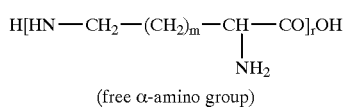

(free α-amino group)

and in each carrier molecule of general formula (I/a) there are monomeres of the same configuration (i.e. either D-, or L-), and the individual monomeres are not linked together by their amino groups in the α-positions, but by their in other amino groups (i.e. in β-, γ-, δ-, ε etc.) positions, according to the value of "m", and their structures are therefore divergent from those of the polypeptides build up by customary α-amino-peptide bonds, generally occurring in mammal organisms;

wherein:
"r" is a mean value between 20 and 400;
"m"=0, 1, 2, 3, . . . k;
"[(k)Mx]" designates enhancer molecules and/or connecting molecules conjugated by covalent (═k) bonds to the isopolypeptide polycation carrier molecule, and
"[(i)Mx]" designates enhancer molecules conjugated by ionic (═i) bonds to the isopolypeptide polycation carrier molecule, whereas the said enhancer molecules and connecting molecules having appropriate functional groups for conjugation may either be identical ones or of (two or more i.e. "x") different kind and the enhancer molecules can be conjugated
directly and/or
indirectly through a connecting molecule,
and further the joint occurrence of [(k)Mx] and [(i)Mx] within the same polycation bioconjugate is symbolized by [(k/i)Mx]. On the basis of the general formula (I) of the new polycation bioconjugates according to the invention further molecules of general formulae (II), (III), (IV), (VI), (VII), (IX), (X), (XI) and of schematic formulae (V), (VIII), (IX/a), (X/a), (XI/a) can be derived.

In case the [$Ex_i$] enhancer molecules—which may either be identical ones or of (two or more i.e. "x") different kind—are directly conjugated to a given representative of carrier molecules of general formula (I/a), by covalent bonds, then:

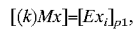

and the new polycation bioconjugates are being described by the general formula (II):

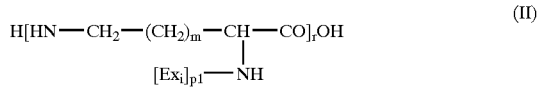

In case the [$(-)Cx_j$] connecting molecules of exclusively anionic character—which may either be identical ones or of (two or more i.e. "x") different kind—are conjugated to a given representative of carrier molecules of general formula (I/a), by covalent bonds, an additional possibility arises to establish ionic bonds with cations—which may either be identical ones or of (two or more i.e. "x") different kind—and then:

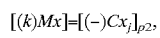

and the new conjugates are being described by the general formula (III):

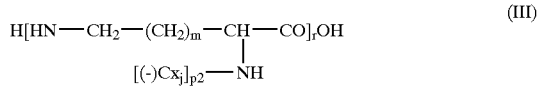

In case the [$Ex_{ek}$] enhancer molecules—which may either be identical ones or of (two or more i.e. "x") different kind—are indirectly conjugated by covalent bonds to a given representative of carrier molecules of general formula (I/a), through [$Cx_{ck}$] connecting molecules—which may also be either identical ones or of (two or more i.e. "x") different kind—then:

and the new polycation bioconjugates are being described by the general formula (IV):

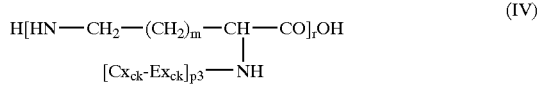

In the case when [$Ex_i$] and/or [$Cx_{ck}-Ex_{ek}$] enhancer molecules and/or [$(-)Cx_j$] connecting molecules of anionic character are also conjugated to a given representative of carrier molecules of general formula (I/a), and furthermore from among "$p_1$, $p_2$ and $p_3$" the value of at least two are greater than 0, then:

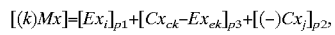

and the new polycation bioconjugates are being described by the schematic formula (V):

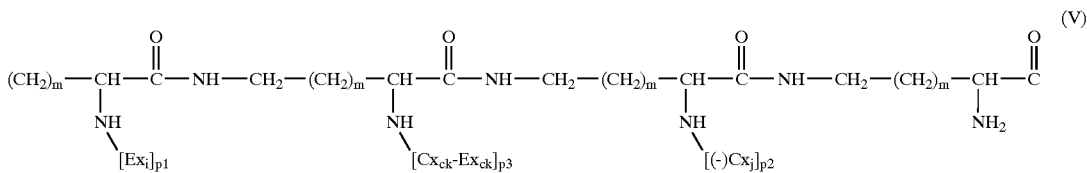

wherein:
- "Ex" in $[Ex_i]_{p1}$ designates the Ex enhancer molecules of different ("x") kind conjugated directly to a given representative of carrier molecules of general formula (I/a), by covalent bonds, and
- "i" indicates whether the Ex enhancer molecules, conjugated to the given carrier molecule by covalent bonds, are identical ones (i=1), or they are of different kind, of number "i" (i=2, 3, . . . "x" kind); and
- "(−)Cx" in $[(-)Cx_j]_{p2}$ designates (−)Cx connecting molecules of exclusively anionic character, of different ("x") kind conjugated to a given representative of carrier molecules of general formula (I/a) by covalent bonds, in order to make it capable for establishing ionic bonds with cations, and
- "j" indicates whether the (−)Cx connecting molecules, conjugated to the given carrier molecule by covalent bonds, are identical ones (j=1), or they are of different kind, of number "j" (j=2, 3, . . . "x"); and "Cx-Ex" in $[Cx_{ck}-Ex_{ek}]_{p3}$ designates the Ex enhancer molecules of different ("x") kind, conjugated by covalent bonds indirectly, through Cx connecting molecules of different ("x") kind, and these Cx molecules are also conjugated by covalent bonds to a given representative of carrier molecules of general formula (I/a), and
- "ck" indicates whether the Cx connecting molecules, conjugated to a given carrier molecule by covalent bonds, are identical ones (ck=1), or they are of different kind, of the number "ck" (ck=2, 3, . . . "x"), and these Cx connecting molecules—practically depending on the structure of the Ex enhancer molecules—may be neutral and/or of anionic and/or of cationic character,
- "ck" indicates whether the Ex enhancer molecules, conjugated to a given carrier molecule indirectly through "Cx" connecting molecules by covalent bonds, are identical ones (ek=1), or they are of different kind, of the number "ck" (ek=2, 3, . . . "x").

Furthermore the degree of saturation in % of a given representative of carrier moleculea of general formula (I/a) by $[Ex_i]_{p1}$ and/or $[Cx_{ck}-Ex_{ek}]_{p3}$ enhancer molecules and/or $[(-)Cx_j]_{p2}$ connecting molecules are given by the different values of "$p_1$, $p_2$ and $p_3$", whereas the summarized value of "$p_1+p_2+p_3$" within one given polycation bioconjugate is >0 and ≦100; whereby the ratio between the free (not involved in peptide bonds) and bound $NH_2$-groups is determined, which in turn influences the charge and the cationic character of the polycation bioconjugates; and thus
- "$p_1$" indicates a degree of saturation in % of a carrier molecule of general formula (I/a) with $[Ex_i]$ enhancer molecules,
- "$p_2$" indicates a degree of saturation in % of a carrier molecule of general formula (I/a) with $[(-)Cx_j]$ connecting molecules of exclusively anionic character,
- "$p_3$" indicates a degree of saturation in % of a carrier molecule of general formula (I/a) with $[Cx_{ck}-Ex_{ek}]$ enhancer molecules which are bound to connecting molecules, and on the basis of the above, in the schematic formula (V) "$p_1+p_2+p_3$">0 and ≦100, and from among "$p_1$, $p_2$ and $p_3$" the value of at least two are greater than 0; further in a given polycation bioconjugate, the Ex molecules in $[Ex_i]$ and the (−)Cx molecules in $[(-)Cx_j]$ are not necessarily identical with those Ex and Cx molecules occurring in $[Cx_{ck}-Ex_{ek}]$, which divergence is symbolized by "x", and will be dealt with later at the examples of suitably selected enhancer molecules, further "r" and "m" have the same meaning as in general formula (I).

In case the $[(-)Ax_s]$ enhancer molecules of anionic character—which may either be identical ones or of (two or more i.e. "x") different kind—are directly conjugated by ionic bonds to the free α-amino groups of a given representative of carrier molecules of general formula (I/a), then:

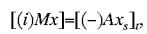

and the new polycation bioconjugates are being described by the general formula (VI):

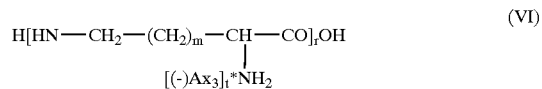

In case the $[(+)Kx_u]$ enhancer molecules of cationic character—which may either be identical ones or of (two or more i.e. "x") different kind—are conjugated directly through $[(-)Cx_j]$ connecting molecules of exclusively anionic character—which may either be identical ones or of (two or more i.e. "x") different kind—by ionic bonds to a given representative of conjugates of general formula (III), then:

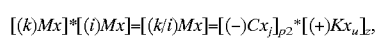

and the new polycation bioconjugates are being described by the general formula (VII):

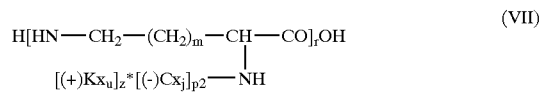

In case additional $[(-)Ax_s]$ enhancer molecules of anionic character—which may either be identical ones or of (two or more i.e. "x") different kind—are conjugated directly by ionic bonds to the free α-amino groups of a given representative of polycation bioconjugates of general formula (VII), then:

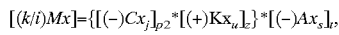

and the new polycation bioconjugates are being described by the schematic formula (VIII):

character—which may either be identical ones or of (two or more i.e. "x") different kind—can be conjugated by ionic bonds to it, then:

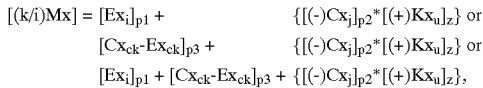

and the polycation bioconjugates are being described by the general formula (X), or by the schematic formula (X/a):

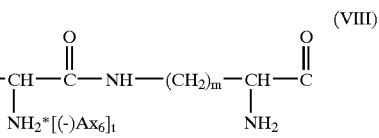

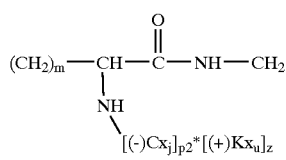

In case additional $[(-)Ax_s]$ enhancer molecules of anionic character—which may either be identical ones or of (two or more i.e. "x") different kind—are conjugated by ionic bonds to the free α-amino groups of a given representative of polycation bioconjugates of general formula (II) or (IV) or of schematic formula (V), then:

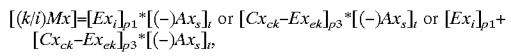

and the new polycation bioconjugates are being described by the general formula (IX), or by the schematic formula (IX/a):

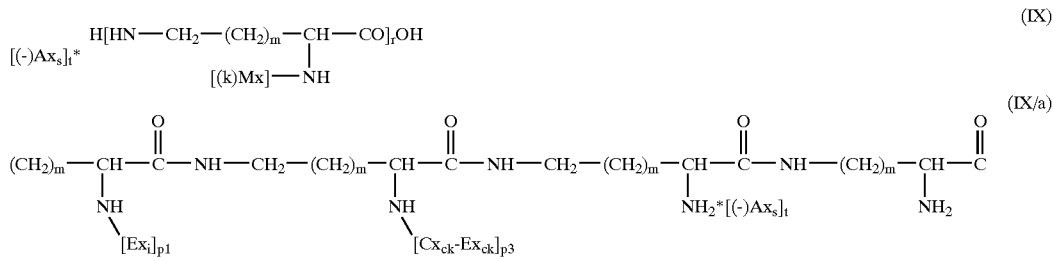

In case a given representative of polycation bioconjugates of schematic formula (V), in which there are $[(-)Cx_j]$

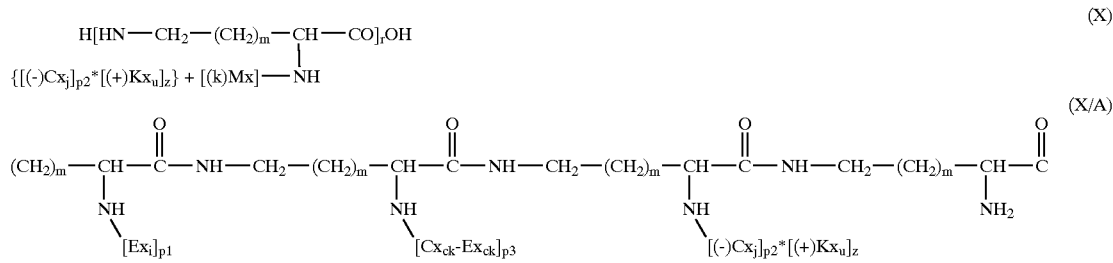

connecting molecules of anionic character—which may also be either identical ones or of (two or more i.e. "x") different kind—and it thus gains partially anionic character, so that additional $[(+)Kx_u]$ enhancer molecules of cationic In case additional $[(-)Ax_s]$ enhancer molecules of anionic character—which may either be identical ones or of (two or more i.e. "x") different kind—are conjugated directly by ionic bonds to the free α-amino groups of a given representative of polycation bioconjugates of general formula (X), then:

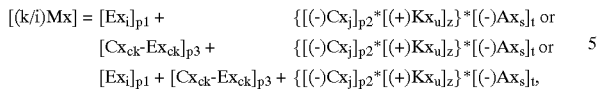

and the polycation bioconjugates are being described by the general formula (XI), or by the schematic formula (XI/a):

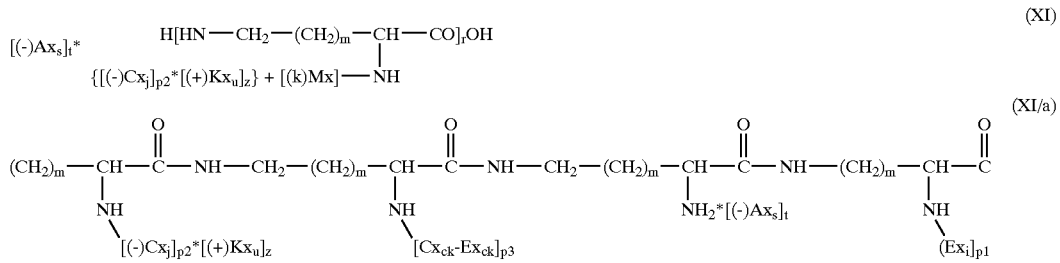

wherein:
"(−)Ax" in [(−)Ax$_s$]$_t$ designates the (−)Ax enhancer molecules of anionic character, of different ("x") kind conjugated directly to a given representative of carrier molecules of general formula (I/a), by ionic bonds, and "s" indicates whether the (−)Ax anionic/polyanionic molecules, conjugated to a given polycation carrier molecule by ionic bonds, are identical ones (s−1), or, they are of different kind, of number "s" (s=2, 3, . . . "x" kind), and "(+)Kx" in [(+)Kx$_u$]$_z$ designates (+)Kx enhancer molecules of different ("x") kind of cationic character that are conjugated indirectly by ionic bonds, through [(−)Cx$_j$] connecting molecules of different ("x") kind of anionic character, to a given representative of carrier molecules of general formula (I/a), that is essentially to a conjugate of general formula (III), and "u" indicates whether the (+)Kx cations and/or polyations, conjugated to a given compound of general formula (III) by ionic bonds, are identical ones (u=1), or they are of different kind of number "u" (u=2, 3, . . . "x" kind), and furthermore "t" indicates a degree of saturation in % of a carrier molecule of general formula (I/a) with [(−)Ax$_s$] enhancer molecules, and "z" indicates a degree of saturation in % of a polycation bioconjugate general formula (I), or a carrier molecule of general formula (I/a) with [(+)Kx$_u$] enhancer molecules, which are conjugated indirectly through [(−)Cx$_j$] connecting molecules of anionic character, and "t" in general formula (VI), and "z" in general formula (VII), and "t"+"z" in schematic formula (VIII), and "t"+"p$_1$" or "t"+"p$_3$" or "t"+"p$_1$"+"p$_3$" in general formula (IX) and in schematic formula (IX/a), and "z"+"p$_1$" or "z"+"p$_3$" or "z"+"p$_1$"+"p$_3$" in general formula (X) and in schematic formula (X/a), and "t"+"z"+"p$_1$" or "t"+"z"+"p$_3$" or "t"+"z"+"p$_1$"+"p$_3$" in general formula (XI) and in schematic formula (XI/a), and the value of each of these sums is between >0 and ≦100; furthermore according to these the NH$_2$-groups which are not saturated by "t" and/or "z" and/or "p$_3$" and/or "p$_3$" will remain free, whereby the ratio between the free (not involved in chemical bonds) and bound NH$_2$-groups is determined, which in turn influences the charge and the cationic character of the polycation bioconjugates, whereas "z" indicates the degree of saturation of carrier molecules with [(+)Kx$_u$] cationic enhancer molecules that are conjugated indirectly through [(−)Cx$_j$] connecting molecules, therefore "z"= "p$_2$"; furthermore "r" and "m" and "[(k)Mx]" have the same meaning as in general formula (I), "[Ex$_i$]$_{p1}$" has the same meaning as in general formula (II), "[(−)Cx$_j$]$_{p2}$" has the same meaning as in general formula (III), "[Cx$_{ck}$-Ex$_{ek}$]$_{p3}$" has the same meaning as in general formula (IV).

Novelty of the polycation bioconjugates of general formula (I), subject of the present invention, consists in that there are isopolypeptides having free α-amino groups, as polycation carrier molecules in them, the synthesis of which is being carried out by coupling the diamino-monocarbonic acid monomers that build up these isopolypeptides, not by their amino groups in α-positions, but their amino groups in other (β-, γ-, γ-, ε- . . . etc.) positions, and the method used for preparation of these carrier molecules has been disclosed in the patent specification HU 202553 B, with the priority of Oct. 10, 1987, titled: "Process for preparation of isopolypeptides from diamino-monocarbonic acids and of drugs containing them, and a plant protection agent containing polyisolysine", further in the paper of Szókan et al.: "Structure Determination and Synthesis of Lysine Isopeptides Influencing on Cell Proliferation" (Biopolymers, J. Wiley & Sons, Inc. 42:305–318, 1997).

To a given representative of carrier molecules of general formula (I/a) within the new polycation bioconjugates of general formula (I), prepared according to the invention, practically any organic and/or inorganic molecule having functional groups appropriate for conjugation can be coupled as a suitably selected enhancer molecule, in accordance with the method shown by general formulae (II), (III), (IV), (VI), (VII), (IX), (X), (XI) and by schematic formulae (V), (VIII), (IX/a), (X/a), (XI/a). All these enhancer molecules can favourably be chosen—with a non-limiting manner—from the group of compounds listed hereinbelow:

hormones and hormone antagonists of different kind (steroid, protein, peptide, etc.), and active fragments of peptide hormones, and derivatives thereof;

saturated and unsaturated fatty acids, cholesterols, phospholipides (phosphoglycerides, sphingomyelins, etc.), and derivatives thereof;

nucleic acids/antisense nucleotides;

monosaccharides, oligosaccharides, and polysaccharides, and derivatives thereof;

vitamines, and their derivatives;

known antitumor drugs and active substances, and derivatives thereof, amino acids, oligopeptides, polypeptides, further glycoproteins and lipoproteins, their fragments, and derivatives thereof.

The new polycation bioconjugates of general formula (I) prepared according to the method described in the invention, contain carrier molecules of general formula (I/a), and a given representative of these carrier molecules is conjugated by chemical (covalent and/or ionic) bonds with enhancer molecules, which are suitably selected, according to the intended effect (for example antiproliferative, antimicrobial, gene delivery, improving of the quality of the diagnostic magnetic resonance imaging, etc.), and these enhancer molecules may either be identical ones or of (two or more i.e. "x") different kind, and due to the applicability of multiple enhancer molecules in a given polycation bioconjugate of general formula (I), manifold direct and/or indirect effects can be obtained simultaneously. A few examples for the compounds that can favourably be applied to this purpose are listed hereinbelow.

Compounds comprising a part of the direct enhancer molecules—with non-limiting character:

compounds having antiproliferative effects, for example: cytosiatics used in the clinical practice, furthermore cytokines, which influence the division and differentiation of the cells (for example different growth factors, as well as antibodies produced against the receptors of these factors, interferons, etc.), furthermore peptides/proteins which inhibit the formation of new blood-vessels around the tumor cells (angiostatins, endostatins), furthermore nucleic acids/antisense oligonucleotides exerting antiproliferative effects on the malignantly transformed cells;

compounds having antimicrobial effects, for example: antiviral, antibacterial, antimycotical, antiprotozooneal, etc. compounds, used in the clinical practice, furthermore nucleic acids/complexed antisense oligonucleotides, which inhibit the replication of the microbes;

nucleic acids isolated or synthetized for the purpose of gene transfer, which are suitable for treating genetic diseases (for example cystic fibrosis);

compounds improving the quality of the diagnostic magnetic resonance imaging, for example: paramagnetic metal ions and complexes containing metal ions of that kind, especially molecule complexes of gadolinium (Gd) ion (for example dimeglumine salt of Gd-diethylene-triamine-pentaacetic acid);

compounds having immunomodulant effects (for example interleukins, tumor necrosis factors, etc.) which control a given function of the immune system; and numerous suitably selected compounds with other effects, not defined herein, that can be used with definite purposes, as enhancer molecules.

Compounds comprising a part of the indirect enhancer molecules, which develop or increase selectivity—with non-limiting character:

in relation to the antiproliferative effects, for example: monoclonal antibodies having specific affinities to a surface antigen of a given tumor cell, as well as antibodies or any compound having affinity to those kind of receptors (for example transferrin receptor or folate receptor among the vitamins, etc.) which are present in a greater ratio on the surface of the tumor cells than of the normal (not malignantly transformed) cells;

furthermore in the relation to the antiproliferative and any other effects, aimed at, any compound which has specific affinity to a certain receptor occurring exclusively on the surface of a given normal cell only (this receptor does not exsist as a result of a pathological process), namely for example the asialoglycoprotein cell surface receptors of the hepatic cells (to which specifically links the terminal galactose of the macromulecules), or any other compound coupling receptors, which are present in greater ratio on the surface of a given target cells;

in general compounds which may link to a given target cell (for example microbes or infected cells with microbes, etc.) to achieve indirect enhancer effect.

Compounds comprising a part of the direct and simultaneously indirect enhancer molecules, with non-limiting character:

in relation to the antiproliferative effects, for example: hormones, hormone antagonists and derivatives thereof, especially from among the polypeptide hormones the humane choriogonadotropine hormone, which having antiproliferative effects, furthermore antibodies produced against receptors of growth factors of different kind, which are present in greater ratio on the surface of a given tumor cell than on other cells, and simultaneously exert antiproliferative effects towards given malignantly transfomed cells, furthermore immmunotoxines, which are produced against a given tumor cell;

in relation to the antimicrobial effects, for example; neutralizing antibodies which are produced against a given microbes (for example viruses, bacteriums, funguses, etc.), furthermore immunotoxines, which are produced against a given microbe.

New polycation bioconjugates of general formula (I) prepared according to the invention contain carrier molecules of general formula (I/a), and a given representative of these carrier molecules is conjugated with enhancer molecules—which may either be identical ones or of (two or more i.e. "x") different kind—that are suitably selected according to the above mentioned examples, and the conjugation of these enhancer molecules are symbolized by $[Ex_i]_{p1}$ and/or $[\ldots -Ex_{ek}]_{p3}$ which indicates that the molecules are coupled by covalent bonds, furthermore $[(-)Ax_s]_t$ having anionic character and/or $[(+)Kx_u]_z$ having cationic character indicate the molecules that are coupled by ionic bonds.

New polycation bioconjugates of general formula (I) prepared according to the invention contain carrier molecules of general formula (I/a), and a given representative of these carrier molecules is conjugated with enhancer molecules—which may either be identical ones or of (two or more i.e. "x") different kind—that are suitably selected according to the above mentioned examples, and the enhancer molecules can be conjugated directly and/or indirectly through connecting molecules, and the latter can couple enhancer molecules covalently or ionically, symbolized by $[Cx_{ck}- \ldots ]_{p3}$ of the covalent ones, and by $[(-)Cx_j]_{p2}$ of the ionic ones, respectively, and these connecting molecules may suitably be chosen—with non-limiting character—from dicarbonic acids, tricarbonic acids, carbohydrates, or amino acids, or peptide chain elongators.

New polycation bioconjugates of general formula (I) prepared according to the invention contain carrier molecules of general formula (I/a), and a given representative of these carrier molecules is conjugated with enhancer molecules—which may either be identical ones or of (two or more i.e. "x") different kind—that are suitably selected according to the above mentioned examples, and the conjugation of the enhancer molecules by covalent and/or ionic chemical bonds takes place directly and/or indirectly, in a determined ratio, preferably to reach a saturation of 10 to 100%.

Preferred representatives of carrier molecules of general formula (I/a) within the new polycation bioconjugates of general formula (I), according to the invention include those 60–120 membered, non-racemic polyiso-L-lysines, i.e. poly (ε)-L-lysine-hydrogen-bromides which themselves possess certain antiproliferative and antiviral effects, as it is disclosed in the patent specification HU 202553 B, of the Hungarian priority of Oct. 21, 1987.

Subject of the invention is the recognition that each of the new polycation bioconjugates of general formula (I), prepared according to the method described in the present invention, contains carrier molecules of general formula (I/a), and these carrier molecules (which themselves possess certain antiproliferative effects) are conjugated by chemical bonds with compounds having antiproliferative effects (some compounds, suitably selected to this purpose are listed above among the direct enhancer molecules), and the bioconjugates so obtained, are being successfully applicable for the treatment of malignancies, developing in mammal organisms (further: tumors), in se, or combined with known tumor-inhibiting methods, accepted in the clinical practice.

The additional enhancer molecules, resulting in developing an appropriately chosen selectivity, that have particularly been disclosed hereinabove (among the indirect enhancer molecules), linked to the bioconjugates prepared according to the invention, are increasing the concentration of active substances in the tumors, whereby the unwanted side-effects can be diminished, and thus the effectiveness of the treatment may further be increased.

Conjugates similar to those new polycation bioconjugates of antiproliferative effect, according to the present invention, have already been prepared earlier. Papers have also been published about them, from among which we would refer to some as follows hereinbelow:

Bogdanov-A. A Jr., Martin-C., Bogdanova-A. V. et al.: An adduct of cis-diamine-dichloroplatinum(II) and poly (ethylene glycol)poly(L-lysine)-succinate: synthesis and cytotoxic properties; *Bioconjug-Chem. January–February* 1996; 7(1): 144–9.

Di-Stefano-G., Busi-C., Derenzini-M. et al.: Conjugation of 5-fluoro-2'-deoxyuridine with lactosaminated poly-l-lysine to reduce extrahepatic toxicity in the treatment of hepatocarcinomas; *Ital-J-Gastroenteral-Hepatol.* April 1998; 30(2): 173–7.

Paprocka-M., Boratynski-J., Dus-D. et al.: Conjugation of the monoclonal antibody 17-1A with the nitroacridine compound C921 with the poly-L-lysine as an intermediate agent; *Arch-Immunol-Ther-Exp-Warsz.* 1997; 45(4): 343–9.

Salazar-A. M., Levy-H. B., Ondra-S. et al.: Long-term treatment of malignant gliomas with intramuscularly administered polyinosinic-polycytidylic acid stabilized with polylysine and carboxymethylcellulose: an open pilot study; *Neurosurgery. June* 1996; 38(6): 1096–103: *discussion* 1103–4.

Another recognition contained in the present invention is the feature or the carrier molecules of general formula (I/a), in the new polycation bioconjugates of general formula (I), that as being polycations, they are appropriate for transporting of, as well as introducing to the target cells the suitably selected nucleic acids of polyanionic character, as enhancer molecules, bound to them by ionic bonds, i.e. for gene transfer, using the effect that by conjugating further enhancer molecules by covalent bonds—details of which see hereinabove—resulting in developing an appropriately chosen selectivity, the new polycation bioconjugates are being linked selectively to the target cells, or in essentially higher ratio to them than to cells of other type.

Conjugates similar to those new polycation bioconjugates, according to the present invention, capable of gene transfer, have already been prepared earlier. Papers have been published about them in the scientific literature, from among which we would refer to some publications—as examples—hereinbelow:

Erbacher-P., Roche-A. C., Monsigny-M., Midoux-P.: The reduction of the positive charges of polylysine by partial gluconoylation increases the transfection efficiency of polylysine/DNA complexes; *Biochim. Biophys. Acta.* Feb. 21, 1997; 1324(1): 27–36.

Ferkol-T., Perales-J. C., Mularo-F., Hanson-R. W.: Receptor-mediated gene transfer into macrophages; *Proc-Natl-Acad-Sci-USA.* Jan. 9, 1996; 93(1): 101–5.

Kollen-W., Erbacher-P., Midoux-P. et al.: Glycosylated polylysines. Nonviral vectors for gene transfer into cystic fibrosis airway epithelial cells; *Chest.* June 1997; 111(6 Suppl): 95S–96S.

Liang-W. W., Shi-X., Deshpande-D. et al.: Oligonucleotide targeting to alveolar macrophages by mannose receptor-mediated endocytosis; *Biochim-Biophys-Acta.* Mar. 13, 1996; 1279(2): 227–34.

Schneider-H., Huse-K., Birkenmeier-G. et al.: Gene transfer mediated by alpha2-macroglobulin; *Nucleic-Acids-Res.* Oct. 1, 1996; 24(19): 3873–4.

Schwarzenberger-P., Spence-S. E., Gooya-J. M. et al.: Targeted gene transfer to human hematopoietic progenitor cell lines through the c-kit receptor; *Blood.* Jan. 15, 1996; 87(2): 472–8.

Sosnowski-B. A, Gonzalez-A. M., Chandler-L. A. et al.: Targeting DNA to cells with basic fibroblast growth factor (FGF2); *J-Biol-Chem.* Dec. 27, 1996; 271(52): 33647–53.

Stewart-A. J., Pichon-C., Meunier-L. et al.: Enhanced biological activity of antisense oligonucleotides complexed with glycosylated poly-L-lysine; *Mol-Pharmacol.* December 1996; 50(6): 1487–94.

Furthermore the new polycation bioconjugates which are suitable for gene transfer in the case of further conjugation with compounds having antiproliferative effects (the suitably selected compounds, detailed among the direct enhancer molecules) are suitable for more effective treatment of the tumors. Scientific reprints have been also published about these, from among which we refer to some as follows hereinbelow:

Cristiano-R. J., Roth-J. A. :. Epidermal growth factor mediated DNA delivery into lung cancer cells via the epidemal growth factor receptor; *Cancer-Gene-Ther.* January–February 1996; 3(1): 4–10.

Foster-B. J., Kern-J. A.: HER2-targeted gene transfer; *Hum-Gene-Ther.* Apr. 10, 1997; 8(6): 719–27.

Ginobbi-P., Geiser-T. A., Ombres-D., Citro-G.: Folic acid-polylysine carrier improves efficacy of c-myc antisense oligodeoxynucleotides on human melanoma (M14) cells; *Anticancer-Res.* January–February 1997; 17(1A): 29–35.

Nguyen-D. M., Wiehle-S. A., Roth-J. A., Cristiano-R. J.: Gene delivery into malignant cells in vivo by a conjugated adenovirus/DNA complex; *Cancer-Gene-Ther.* May–June 1997; 4(3): 183–90.

Schachtschabel-U., Pavlinkova-G., Lou-D., Kohler-H.: Antibody-mediated gene delivery for B-cell lymphoma in vitro; *Cancer-Gene-Ther*. November–December 1996; 3(6): 365–72.

Shimizu-N., Chen-J., Gamou-S., Takayanagi-A.: Immunogene approach toward cancer therapy using erythrocyte growth factor receptor-mediated gene delivery, *Cancer-Gene-Ther*. March–April 1996; 3(2): 113–20.

Watanabe-N., Sato-Y., Yamauchi-N., Niitsu-Y.: Gene delivery into human cancer cells via transferrin receptor; *Nippon-Rinsho*. March 1998; 56(3): 724–30.

Another recognition also belongs to the subject of the present invention, namely that each of the new polycation bioconjugates of general formula (I) prepared according to the method described in the invention, contains carrier molecules of general formula (I/a) and these carrier molecules (which possess certain antiviral effects themselves) are conjugated, by chemical bond, with suitably selected compounds having antiviral effects, as direct enhancer molecules, and due to this increase the antiviral effect of the new polycation bioconjugates.

New polycation bioconjugates which are produced in the way described in the paragraph before, conjugated furthermore, by chemical bond, with suitably selected compounds which develop or increase selectivity to the target cells which are infected by the virus (the suitably selected compounds detailed among the indirect enhancer molecules) are suitable to increase the relative concentration of the new antiviral character polycation bioconjugates in the cells which are infected by the virus and due to it the efficacy of the treatment will be increased and side-effects greatly diminished. Conjugates similar to those new polycation bioconjugates of antiviral effect, according to the present invention, have already been prepared earlier. Papers have also been published about them, from among which we would refer to some as follows hereinbelow:

Di-Stefano-G., Colonna-F. P., Bongini-A. et al.: Ribavirin conjugated with lactosaminated poly-L-lysine: selective delivery to the liver and increased antiviral activity in mice with viral hepatitis; *Biochem-Pharmacol*. Aug. 1, 1997; 54(3): 357–63.

Fiume-L., Di-Stefano-G., Busi-C. et al.: Liver targeting of antiviral nucleoside analogues through the asialoglycoprotein receptor; *J-Viral-Hepat*. 1997: 4(6): 363–70.

Fiume-L; Di-Stefano-G; Busi-C. et al.: Hepatotropic conjugate of adenine arabinoside monophosphate with lactosaminated poly-L-lysine. Synthesis of the carrier and pharmacological properties of the conjugate; *J-Hepatol*. February 1997; 26(2): 253–9.

Nakazono-K., Ito-Y., Wu-C. H., Wu-G. Y.: Inhibition of hepatitis B virus replication by targeted pretreatment of complexed antisense DNA in vitro; *Hepatology*. June 1996: 23(6): 1297–303.

Another recognition also belongs to the subject of the present invention, namely that each of the new polycation bioconjugates of general formula (I) prepared according to the method described in the invention, contains carrier molecules of general formula (I/a) and these carrier molecules are conjugated, by chemical bond, with compounds having different kind of antimicrobial effects (the suitably selected compounds, detailed among the direct enhancer molecules), and due to this, the new polycation bioconjugates significantly increase the antimicrobial effects surpassing the antiviral character, which was described in the three previous paragraph.

New polycation bioconjugates which are produced in the way described in the paragraph before, conjugated furthermore, by chemical bond, with compounds which develop or increase selectivity to the target cells which are infected by different kind of microbas (the suitably selected compounds, detailed among the indirect enhancer molecules) are suitable to increase the relative concentration of the antimicrobial character polycation bioconjugates in the cells which are infected by the given microbas and due to this the efficacy of the treatment will be increased and side-effects greatly diminished.

Another recognition also belongs to the subject of the present invention, namely that each of the new polycation bioconjugates of general formula (I) prepared according to the method described in the invention, contains carrier molecules of general formula (I/a) and these carrier molecules are conjugated, by chemical bond, with macromolecular paramagnetic contrast agents for example the gadolinium molecule complexes, and derivatives thereof, (the suitably selected compounds, detailed among the direct enhancer molecules), and due to this, the new polycation bioconjugates significantly improve the quality of the diagnostic magnetic resonance imaging, by increasing the contrast between the different kind of organs, tissues, as well as the different pathological alterations, for example tumors.

New polycation bioconjugates which are produced in the way described in the paragraph before, conjugated furthermore, by chemical bond, with compounds which develop or increase selectivity to the different kind of target organs or different pathological alterations (the suitably selected compounds, detailed among the indirect enhancer molecules), are suitable to increase significantly the relative concentration of the paramagnetic contrast character polycation bioconjugates in the different kind of organs, tissue, as well as, the different pathological alterations, and due to this further improve the quality of the magnetic resonace imaging.

Conjugates similar to those new polycation bioconjugates of paramagnetic character, according to the present invention, have already been prepared earlier. Papers have also been published about them, from among which we would refer to some as follows hereinbelow:

Opsahl-L. R, Uzgiris-E. E., Vera-D. R.: Tumor imaging with a macromolecular paramagnetic contrast agent:gadopentetate dimeglumine-polylysine; *Acad-Radiol*. September 1995; 2(9): 762–7.

Su-M. Y., Muhler-A., Lao-X., Naleioglu-O.: Tumor characterization with dynamic contrast-enhanced MR1 using MR contrast agents of various molecular weights; *Magn-Reson-Med*. February 1998; 39(2): 259–69.

Vera-D. R., Buonocore-M. H., Wisner-E. R. et al.: A molecular receptor-binding contrast agent for magnetic resonance imaging of the liver, *Acad-Radiol*. June 1995; 2(6): 497–506.

Vogl-T. J., Hoffmann-Y., Juergens-M. et al.: Experimentelle Evaluierung der kontrastmittelverstärken, hochaufl ösenden MR-Angiographie am Tiermodell. Gd-DTPA gegenüber Gd-DTPA-Polylysin; *Radiologie*. March 1996; 36(3): 254–62.

Another recognition also belongs to the subject of the present invention, namely that each of the new polycation bioconjugates of general formula (I) prepared according to the method described in the invention, contains carrier molecules of general formula (I/a) and these carrier molecules as polycations make suitable the polycation bioconjugates to get into the mammal organism, via transdermal transport by iontophoresis.

The new polycation bioconjugates which are trasported through the skin, exert their effects mainly in the different strata of the skin, and in the subcutan tissues, at the area of the iontophoresis, and certain amount of them act systemic. These kind of actions depend on the molecular size, the physico-chemical character and the type of the suitably selected direct and/or indirect enhancer molecule of the polycation bioconjugates, as well as, on the nature of the applied electric field.

The concentration of the new polycation bioconjugates, which are prepared according to the therapeutical aims (for example antiproliferative or antiviral effects, etc.) and which contain the suitably selected and above detailed direct and/or indirect enhancer molecules, increases at the place of the transdermal application, and due to this the local efficacy of the treatment will be greatly increased and side-effects diminished. If the aim is to achieve a systemic effect via transdermal application, the advantage will manifest in a constant, non invasiv administration of the polycation bioconjugates, wich avoid the gastro-intestinal system. Conjugates similar to those new polycation bioconjugates capable of transdermal application, according to the present invention, have already been prepared earlier. Papers have also been published about them, from among which we would refer to some as follows hereinbelow:

Turner-N. G., Ferry-L., Price-M. et al.: Iontophoresis of poly-L-lysines: the role of molecular weight?; *Pharm-Res.* October 1997; 14(10): 1322–31.

Vanbever-R, Prausnitz-M. R., Preat-V.: Macromolecules as novel transdermal transport enhancers for skin electroporation; *Pharm-Res.* May 1997; 14(5): 638–44.

Another recognition also belongs to the subject of the present invention, namely that each of the new polycation bioconjugates of general formula (I) prepared according to the method described in the invention, contains carrier molecules of general formula (I/a), and these carrier molecules are conjugated with above detailed, direct and/or indirect enhancer molecules, which are suitably selected according to a given therapeutical purpose (for example antiproliferative or antiviral effects or gene therapy, etc.), and these new polycation bioconjugates are to be placed into cationic liposomes, and due to this the efficacy of the treatments will be increased and the side-effects greatly diminished. Conjugates similar to those new polycation bioconjugates which are suitable to be placed into cationic liposomes, according to the present invention, have already been prepared earlier. Papers have also been published about them, from among which we would refer to some as follows hereinbelow:

Gao-X., Huang-L: Potentiation of cationic Liposome-mediated gene delivery by polycations; *Biochemistry.* Jan. 23, 1996; 35(3): 1027–36.

Lee-R. J., Huang-L.: Folate-targeted, anionic liposome-entrapped polylysine-condensed DNA for tumor cell-specific gene transfer, *J-Biol-Chem.* Apr. 5, 1996; 271 (14): 8481–7.

Mack-K. D., Walzem-R. L., Lehmann-Bruinsma-K. et al.: Polylysine enhances cationic liposome-mediated transfection of the hepatoblastoma cell line Hep G2; *Biotechnol-Appl-Biochem.* June 1996; 23 (Pt 3): 217–20.

Saldeen-J., Curiel-D. T., Eizirik-D. L. et al.: Efficient gene transfer to dispersed human pancreatic islet cells in vitro using adenovirus-polylysine/DNA complexes or polycationic liposomes; *Diabetes.* September 1996; 45(9): 1197–203.

Vitiello-L., Chonn-A., Wasserman-J. D. et al.: Condensation of plasmid DNA with polylysine improves liposome-mediated gene transfer into established and primary muscle cells; *Gene-Ther.* May 1996: 3(5): 396–404.

Zelphati-O., Szoka-F. C Jr.: Mechanism of oligonucleotide release from cationic liposomes; *Proc-Natl-Acad-Sci-U-S-A.* Oct. 15, 1996; 93(21): 11493–8

The biologically effective conjugates which have been described in the scientific reviewes of medicine, and cited above, contain carrier molecules, which are build up from diamino-monocarbonic acid monomers, namely lysines, that are coupled to each other by peptide bonds through amino groups in the α-positions, therefore as a result of their synthesis, poly-(α)-L-lysine is formed, and these facts support anyway the recognitions of the present invention, indirectly.

On the basis of all above aspects, the novelty of the invention is comprising in that each of the polycation bioconjugates of general formula (I), prepared according to the invention, contains carrier molecules of general formula (I/a), and these carrier molecules are build up from diamino-monocarbonic acid monomers, which are coupled by peptide bonds formed via the amino groups in the (β-, γ-, δ-, ε- . . . , etc.) positions, corresponding to the value of "m", and not through amino groups in the α-position, and therefore, as a result of the synthesis β-, γ-, δ-, ε- . . . , etc. polypeptides are forming, which are structurally entirely different from those polypeptides that have been described in the cited scientific reviews. The biological behaviour of the new polycation bioconjugates of general formula (I) will therefore be altered. For instance, they are more resistant against proteolytic enzymes, further the carrier molecules of general formula (I/a) themselves possess certain antiproliferative, antiviral activity, and as a consequence, the biological, effectiveness of the new polycation bioconjugates of general formula (I) is being modified favourably. The new polycation bioconjugates of general formula (I) according to the invention are being formulated as pharmaceutical preparates that are applicable perorally, parenterally, or transdermally, for systemic or topical use.

Preferred representatives of the new polycation bioconjugates of general formula (I) according to the invention are those bioconjugates, in which the carrier molecules of general formula (I/a) are poly-(ε)-L-lysines, whereas the preparation of some representatives thereof is illustrated by the following examples hereinbelow:

EXAMPLE 1

Preparation of palmitoyl-poly-(ε)-L-lysine-hydrogen-bromide

The reaction scheme:

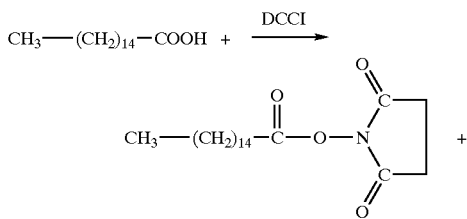

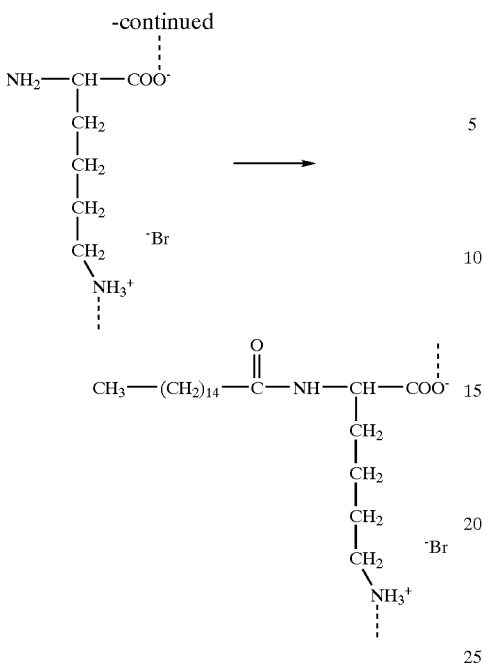

Formula of palmitoyl-poly-(ε)-L-lysine-hydrogen-bromide—according to the general formula (II) of the new polycation bioconjugates of the invention—is:

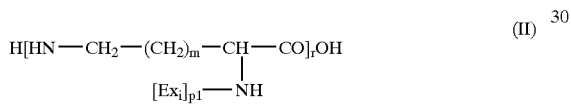

(II)

wherein:
"m"=3, "r"=99±2,
"E"=$CH_3$—$(CH_2)_{14}$—CO—,
"i"=1, i.e. only one single kind of enhancer molecules is being linked by chemical bond to the carrier molecule, and
"$p_1$"=12±2%.
  a) Poly-(ε)-L-lysine-hydrogen-bromide (mean $M_w$=12700±200, specific optical rotation=+32.4°, degree of polymerisation: R=99±2), as a carrier molecule according to the invention, of the general formula (I/a), was synthetized following the method described in Example 1i) of the Hungarian patent specification HU 202553 B.
  b) preparing of palmitoyl-N-hydroxy-succinimide needed to the palmitoylation reaction: 1.28 g (5 mmole) of palmitoic acid and 0.58 g (5 mmole) N-hydroxy-succinimide were dissolved in 12 ml of abs. tetrahydrofurane, and to this solution 1.03 g (5 mmole) of dicyclohexyl-carbodiimide was added, then the mixture was stirred for 4 hours at 0° C., subsequently left standing at +4° C. for 12 hours and the precipitated dicyclohexyl-carbamide that formed during the process was glass-filtered in vacuo and was washed three times with tetrahydrofurane, the clear solution so obtained was concentrated to dryness, the solid residue was dissolved in 100 ml of ethyl acetate, and the latter was washed three times with 5% sodium bicarbonate solution, then three times with water, which resulted in 1.08 g of palmitoyl-N-hydroxy-succinimide end product in white, crystalline form. Its purity was checked by TLC and IR.
  c) 250 mg of poly(ε)-L-lysine-hydrogen-bromide prepared according to the method described in Example 1a) was dissolved in 1.5 ml of water, pH of the solution was adjusted to 8, by adding 1N NaOH, under vigorous stirring, then the solution was cleared up by adding 1.5 ml of tetrahydrofurane and 0.5 ml of dimethyl formamide, and after addition of 50 mg of sodium bicarbonate under vigorous stirring, 28 mg of palmitoyl-N-hydroxy-succinimide, freshly prepared according to Example 1b), and dissolved in 0.2 ml of 6:1 tetrahydrofurane/dimethyl formamide mixture, was added to the reaction mixture, followed by 4 hours of vigorous stirring, while the pH was kept on 8, by dropping 5N sodium hydroxide into the solution, and it was left standing for 12 hours at +4° C., afterwards. Following this 0.1 ml of azeotropic hydrogen bromide solution was added dropwise, then the reaction mixture was poured into an excess (20 ml) of tetrahydrofurane, the precipitate was washed with tetrahydrofurane three–four times, until it became powdery, then the latter was washed two times with diethylether and dried subsequently; the palmitoyl-poly(ε)-L-lysine-hydrogen-bromide end product was obtained this way. The yield was 245 mg. Free amino groups of the product were checked by trinitrobenzene sulfonic acid analysis, according to which the degree of substitution was 12±2%. By increasing the amount of palmitoyl-N-hydroxy-succinimide reactant, the degree of substitution also increased, and reached the necessary % level.

EXAMPLE 2

Preparation of hemisuccinyl-poly-(ε)-L-lysine-hydrogen-bromide

The reaction scheme:

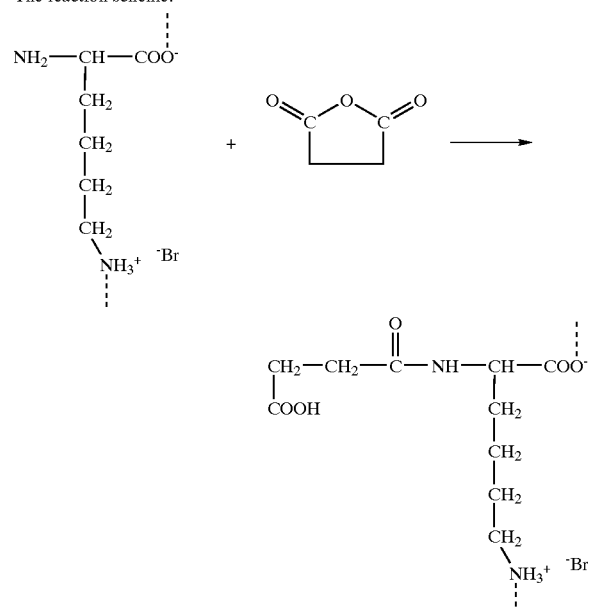

Formula of hydrobromide salt of hemisuccinyl-poly-(ε)-L-lysine—according to the general formula (III) of the new compounds of the invention—is:

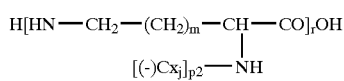

(III)

wherein:
"m"=3, "r"=99±2;
"(-)C"=—OC—CH$_2$—CH$_2$—COOH;
"j"=1; i.e. only one single kind of connecting molecules is being linked by covalent bonds to the carrier molecule, and
p$_2$==20±2%.
  a) Poly-(ε)-L-lysine-hydrogen-bromide, as being a carrier molecule of general formula (I/a) of the invention, was synthetized according to Example 1a) of the present patent application.
  b) 60 mg of poly-(ε)-L-lysine-hydrogen-bromide prepared according to Example 1a) was dissolved in 2 ml of water, and the pH of the solution was adjusted to 8, by adding 1N sodium hydroxyde, under vigorous stirring, then 30 mg of freshly prepared succinic anhydride was added in portions to the solution, in about 40 minutes time, whereas keeping the pH on 8 was accomplished by dropping 5N NaOH, followed by stirring for 40 minutes, additionally, and at the end of the reaction pH of the mixture was lowered to 4.5 by 6N hydrochloric acid, then it was filled into a dialysing bag and has been dialysed against water for 48 hours, subsequently at +4° C. temperature, by changing four times the water, the hemisuccinyl-poly(ε)-L-lysine-hydrogen-bromide salt end product was isolated by freeze-drying. The yield was 46 mg. Free amino groups of the product were checked by trinitro benzene sulfonic acid analysis, according to which the degree of substitution was 20%. By increasing the amount of succinic acid, degree of substitution has also been increased, and reached a proper, necessary % level.

EXAMPLE 3

Preparation of cholesterol-hemisuccinyl-poly-(ε)-L-lysine-hydrogen-bromide

The reaction scheme:

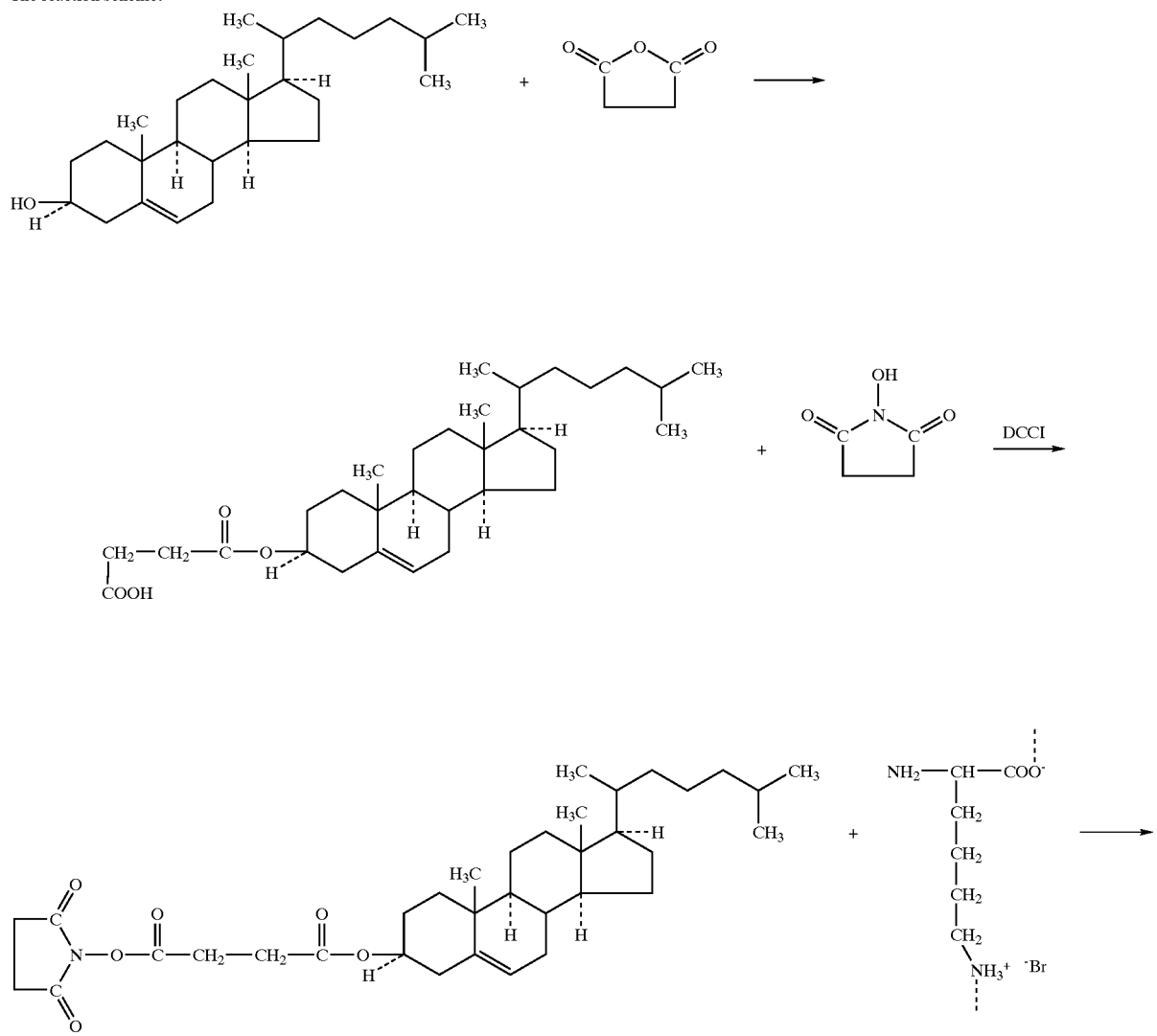

Formula of hydrobromide salt of cholesterol-hemisuccinyl-poly-(ε)-L-lysine—according to the general formula (IV) of the new polycation bioconjugates of the invention—is:

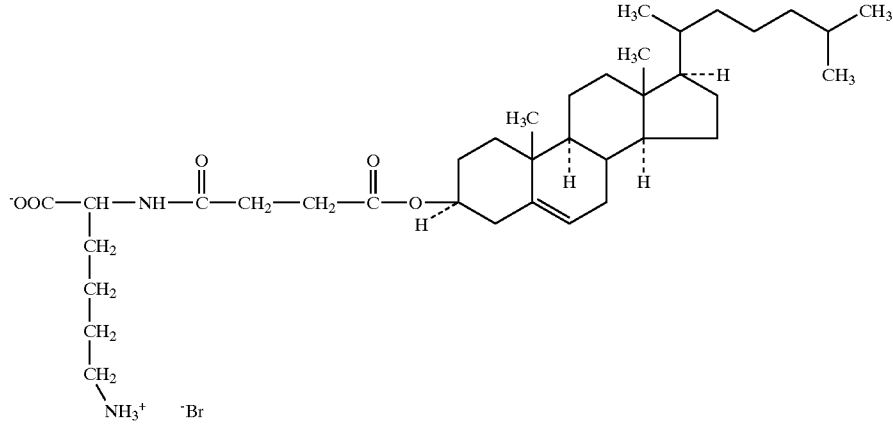

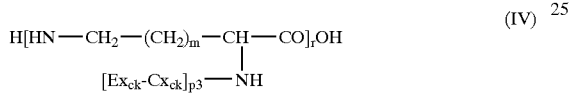

wherein:
"m"=3, "r"=99±2;
"C"=—OC—CH$_2$—CH$_2$—CO—;
"E"=cholesterol;
"ek"="ck"=1: i.e. only one single kind of enhancer and of connecting molecules is being liked by covalent bonds to the carrier molecule, and
"p$_3$"=15±2%.

a) Poly-(ε)-L-lysine-hydrogen-bromide, as being a carrier molecule of general formula (I/a) of the invention, was synthetized according to Example 1a) of the present patent application.
b) preparation of cholesterol-hemisuccinate-N-hydroxy-succinimide ester needed to the conjugation: 0.98 g (2 mmole) of commercially available (e.g. from Sigma) cholesterol-hemisuccinate and 0.23 g (2 mmole) of N-hydroxy-succinimide were dissolved in 10 ml of abs. tetrahydrofurane, 0.41 g (2 mmole) of dicyclohexyl-carbodiimide was then added, and the mixture was stirred at 0° C., for 4 hours, then left standing for 12 hours, and the thus formed precipitate dicyclohexyl-carbamide was glass-filtered in vacuo, washed three times with tetrahydrofurane, and the clear solution so obtained was concentrated to dryness, the solid residue was dissolved in 50 ml of ethyl acetate, and the latter was washed three times with 5% sodium bicarbonate solution, then three times with water. Subsequently it was dried with adding sodium sulfate sicc., followed by washing with ethyl acetate and concentration of the solution. The cholesterol-hemisuccinate-N-hydroxy-succinimide ester end product was obtained in the form of white, crystalline material. The yield was 0.73 g. Purity was checked by TLC and by IR.
c) 240 mg of poly-(ε)-L-lysine-hydrogen-bromide salt synthetized according to Example 3a) was dissolved in 4.8 ml of water and the pH of the solution was adjusted to 8, by 1N sodium hydroxyde, under vigorous stirring, and by adding 1.6 ml of tetrahydrofurane a clear solution was obtained, then 200 mg of sodium bicarbonate was poured into it under vigorous stirring, by adding of 50 mg cholesterol-hemisuccinate-N-hydroxy-succinimide ester, freshly prepared according to Example 3b), dissolved in 2.4 ml tetrahydrofurane, and the solution was kept strongly stirred at room temperature for 4 hours, while keeping the pH at a value of 8 by dropping 5N sodium hydroxyde into the solution. Subsequently it was left standing for 12 hours at +4° C., then 0.3 ml of azeotropic hydrogen bromide was dropped in, and the reaction mixture was poured into an excess (30 ml) of tetrahydrofurane. The precipitate was washed thereafter with tetrahydrofurane three-to-four times, until it became powdery. The latter was washed with diethyl ether two times, dried, and the cholesterol-hemisuccinyl-poly-(ε)-L-lysine-hydrogen-bromide salt end product was obtained this way with 275 mg yield. Free amino groups of the product were checked by trinitro benzene sulfonic acid analysis, according to which the degree of substitution was 15±2%. By increasing the amount of cholesterol-hemisuccinate-N-hydroxy-succinimide ester, the degree of substitution also increased, and reached a proper, necessary % level.

EXAMPLE 4

Preparation of poly-(ε)-L-lysine-cisplatin-hydrogen-bromide

The reaction scheme:

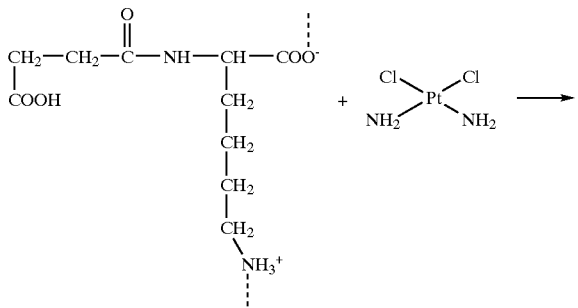

-continued

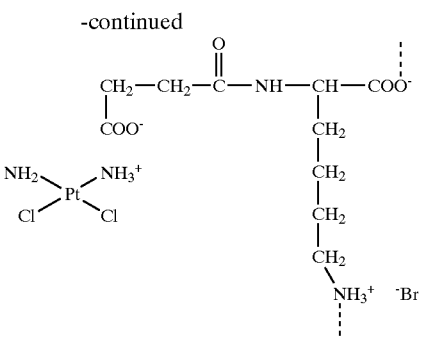

Formula of poly-(ε)-L-lysine-cisplatin-hydrogen-bromide—according to the new polycation bioconjugates of general formula (VII) of the invention—is:

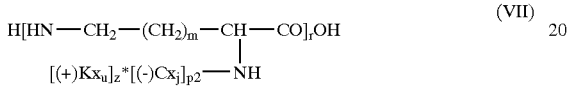

wherein:
"m"=3, "r"=99±2,
"(-)C"=—OC—CH$_2$—CH$_2$—COO$^{31}$,
"(+)K"=cisplatin,
"u"="j"=1; i.e. only one single kind of enhancer and of connecting molecules, respectively are being linked ionic bonds to the carrier molecule, and
"u"="p$_2$"=80±2%.

10 mg cisplatin (Platidiam®, manufacturer: Lachema, Czech Rep.) was dissolved in 3 ml of water and to this solution 23 mg of hemisuccinyl-poly-(ε)-L-lysine-hydrogen-bromide salt of 80% succinylation, prepared according to Example 1 of the present patent application, was added, the solution was left standing for 48 hours at +4° C., then it was filled into a dialysing bag and has been dialysed against water for 48 hours at +4° C. temperature, by changing the water four times, the poly-(ε)-L-lysine-cisplatin-hydrogen-bromide end product was subsequently isolated by freeze-drying. The yield was 15 mg. The Pt-content (i.e. the content of cisplatin) of the product was assayed by atomic absorption spectroscopy, according to which the Pt/Br mass ratio=16; the molar ratio=6.5; the Pt-content=2.7 mg/g; the amount of cisplatin in the poly-(ε)-L-lysine-cisplatin-hydrogen-bromide molecule has been proportional to the degree of succinylation of hemisuccinyl-poly-(ε)-L-lysine-hydrogen-bromide.

BIOLOGICAL EXAMINATIONS

The tumor inhibitory effect of the polycation bioconjugates, which is a part of the subject of the invention, were studied, in vitro, on tumor cell cultures and in vivo, on transplantable rodent tumors. The in vitro inhibitory effect on cell proliferation and the in vivo tumor growth inhibitory effect of the different polycation bioconjugates, prepared according to the invention, was compared to the untreated control ones.

The biological experiments were carried out with the compounds, that were prepared according to the examples No. 1, 2, 3 and 4 of the invention, namely
palmitoyl-poly-(ε)-L-lysine-hydrogen-bromide,
hemisuccinyl-poly-(ε)-L-lysine-hydrogen-bromide,
cholesterol-hemisuccinyl-poly-(ε)-L-lysine-hydrogen-bromide,
poly-(ε)-L-lysine-cisplatin-hydrogen-bromide.

In vitro Experiments

In vitro experiments were carried out with patmitoyl-poly-(ε)-L-lysine-hydrogen-bromide, hemisuccinyl-poly-(ε)-L-lysine-hydrogen-bromide and poly-(ε)-L-lysine-cisplatin-hydrogen-bromide.

Cell lines used in the experiments:

P388 mouse lymphocytic leukemia cell line, originated from Arthur D. Little Inc., Cambridge, Mass., USA, in vitro established in the National Institute of Oncology, Budapest, Hungary (Cancer Treat. Rep. 1986; 70: 279–284);
MCF-7 humane breast cancer cell line, originated from American Type Culture Collection;
PC3 humane prostate cancer cell line, originated from American Type Culture Collection;

Methods used in the in vitro experiments:
1./Clonogenic assay:
MCF-7, or PC3 cells were plated into petri dishes, then in adequate medium and conditions, were incubated the cells with serial dilutions of the different polycation bioconjugates, prepared according to the invention. The colonies, consisting minimum 30 cells were then counted and the obtained values of three parallel petri dishes were averaged. Relative cloning efficiency was calculated by taking the control values as 100 per cent. (Cancer Detection and Prevetion, 20(2): 146–152, 1996).

2./Inhibition of proliferation:
Sulforodamine B (SRB) assay: approximately one to two thousand cells were put into each well of the special, small plastic tray (micro-well-plates). The cells were incubated in adequate medium and conditions and after adhering to the surface, were treated with serial dilutions of the different polycation bioconjugates, prepared according to the invention. At the end of the experiment the cells were fixed, stained with SRB, and the optical density, which is in direct proportion to the cell proliferation, was read in a CLS 962 ELISA microplate reader. Relative inhibition of proliferation was calculated by taking the control values as 100 per cent. (Cancer Detection and Prevention, 20(2): 146–152, 1996).

Cell counting method, with Neubauer-type chamber: in suspension cultures of exponentially growing cells, which were in adequate medium and conditions, were treated with serial dilutions of the different polycation bioconjugates, prepared according to the invention, and 24- and 48 hours following the treatment the cells were stained with tripan-blue, the treated and control cells were counted in a modified Neubauer-type hemocytometer chamber. Relative inhibition of proliferation was calculated by taking the control values as 100 per cent.

In vivo Experiments

The in vivo experiments were carried out with palmitoyl-poly-(ε)-L-lysine-hydrogen-bromide and cholesterol-hemisuccinyl-poly-(ε)-L-lysine-hydrogen-bromide as a monotherapy, and together with Cytoxan® (Bristol-Myers) as combination therapy, and the compounds were administrated in schedules of single or repeated dose therapy, and they were applied intravenously or intraperitoneally.

The tumor growth inhibitory effect of the polycation bioconjugates was studied on the following transpalatable rodent tumors:
P-388 lymphoid leukemia cells, originated from Cambridge, Mass., USA, were transplanted i.p. and s.c. into animals: BDF1 inbred male mice, weighing 22–24 g, specified pathogen free (SPF) breedings;

S-180 sarcoma, originated from Chester Beatty I., London, were transplanted s.c. into animals: BDF1 inbred male mice, weighing 22–24 g, specified pathogen free (SPF) breedings.

Results of the Biological Experiments

In vitro Experiments

On tumor cell cultures, in vitro, the palmitoyl-poly-(ε)-L-lysine-hydrogen-bromide, cholesterol-hemisuccinyl-poly-(ε)-L-lysine-hydrogen-bromide and poly-(ε)-L-lysine-cisplatin-hydrogen-bromide exert a dose dependent inhibition on the colony formation and the cell proliferation, the most effective inhibition have been shown by the palmitoyl-poly-(ε)-L-lysine-hydrogen-bromide, and poly-(ε)-L-lysine-cisplatin-hydrogen-bromide.

In vivo Experiments

On the basis of mean tumor volumes and tumor growth curves we observed a significant inhibitory effect of the palmitoyl-poly-(ε)-L-lysine-hydrogen-bromide and cholesterol-hemisuccinyl-poly-(ε)-L-lysine-hydrogen-bromide on transplantable rodent tumors, furthermore the combined treatment with palmitoyl-poly-(ε)-L-lysine-hydrogen-bromide plus Cytoxan® significantly inhibited the tumor growth and significantly increased the life span of the experimental animals inoculated with tumor, compared to the untreated control, as well as to the animals which were treated only with Cytoxan®.

I claim:

1. A polycation bioconjugate, comprising:

one or more carrier molecules having free α-amino groups, and one or more enhancer or connecting molecules, wherein the polycation bioconjugate has the general formula (I)

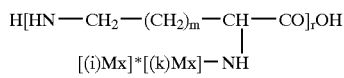

wherein

"r" is a mean value between 20 and 400 that designates the number of diaminomonocarbonic acyl group monomers;

"m"=0, 1, 2, 3, . . . ;

[(k)Mx] designates enhancer molecules and/or connecting molecules linked by covalent (=k) bonds to a carrier molecule;

[(i)Mx] designates enhancer molecules linked by ionic (=i) bonds to a carrier molecule, wherein the Mx functional groups may be the same or different, and the enhancer molecules can be linked directly and/or indirectly, through a connecting molecule, to the carrier molecule, and wherein when both [(k)Mx] and [(i)Mx] occur within the same polycation bioconjugate [(i)Mx]*[(k)Mx] is symbolized by [(k/i)Mx];

the carrier molecules are of the same configuration (either D- or L-), and the individual monomers are not linked together by their amino groups in the α-positions, and are linked together by amino groups in other positions according to the value of m, wherein the carrier molecules have a general formula (I/a):

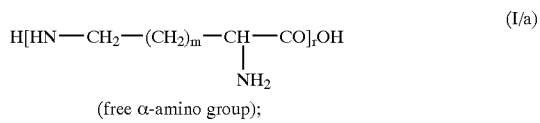

(free α-amino group);

wherein [(k)Mx]=[(-)Cx_j]p_2 and at least one carrier molecule is linked with one or more connecting molecules [(-)Cx_j] of anionic character, wherein the Cx_j molecules may be the same or different, and are selected from the group consisting of dicarbonic acids, tricarbonic acids, carbohydrates, amino acids, and peptide chain elongators; wherein "(-)Cx" in "[(-)Cx_j]p_2" designates (-)Cx connecting molecules of anionic character of different ("x") kind linked to at least one carrier molecule of general formula (I/a) by covalent bonds;

"j" indicates whether the (-)Cx connecting molecules are identical (j=1) or different according to the number "j" (j=2, 3, . . . ); and "p_2" indicates a degree of saturation in % of a carrier molecule of general formula (I/a) by [(-)Cx_j] connecting molecules of exclusively anionic character, p_2 having a value which is >0 and ≤100.

2. The polycation bioconjugate of claim 1, wherein at least one carrier molecule is linked by an ionic bond with an enhancer molecule of cationic character.

3. A polycation bioconjugate, comprising:

one or more carrier molecules having free α-amino groups, and one or more enhancer or connecting molecules, wherein the polycation bioconjugate has the general formula (I)

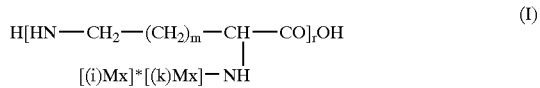

wherein

"r" is a mean value between 20 and 400 that designates the number of diaminomonocarbonic acyl group monomers;

"m"=0, 1, 2, 3, . . . ;

[(k)Mx] designates enhancer molecules and/or connecting molecules linked by covalent (=k) bonds to a carrier molecule;

[(i)Mx] designates enhancer molecules linked by ionic (=i) bonds to a carrier molecule, wherein the Mx functional groups may be the same or different, and the enhancer molecules can be linked directly and/or indirectly, through a connecting molecule, to the carrier molecule, and wherein when both [(k)Mx] and [(i)Mx] occur within the same polycation bioconjugate [(i)Mx]*[(k)Mx] is symbolized by [(k/i)Mx];

the carrier molecules are of the same configuration (either D- or L-), and the individual monomers are not linked together by their amino groups in the α-positions, and are linked together by amino groups in other positions according to the value of m, wherein the carrier molecules have a general formula (I/a):

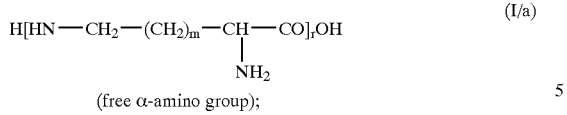

(free α-amino group);

wherein [(k)Mx]=
[Ex$_i$]$_{p1}$ and/or
[(-)Cx$_j$]$_{p2}$ and/or
[Cx$_{ck}$-Ex$_{ek}$]$_{p3}$ and at least one carrier molecule is linked with at least two of [Ex$_i$]$_{p1}$, [(-)Cx$_j$]$_{p2}$ and [Cx$_{ck}$-Ex$_{ek}$]$_{p3}$, such that [(k)Mx]=
[Ex$_i$]$_{p1}$+[(-)Cx$_j$]$_{p2}$ or
[Ex$_i$]$_{p1}$+[Cx$_{ck}$-Ex$_{ek}$]$_{p3}$ or
[Cx$_{ck}$-Ex$_{ek}$]$_{p3}$+[(-)Cx$_j$]$_{p2}$ or
[Ex$_i$]$_{p1}$+[Cx$_{ck}$-Ex$_{ek}$]$_{p3}$+[(-)Cx$_j$]$_{p2}$, wherein "Ex" in "[Ex$_i$]$_{p1}$" designates the Ex enhancer molecules of different ("x") kind linked to at least one carrier molecule of general formula (I/a) by covalent bonds;

"i" indicates whether the Ex enhancer molecules are identical ones (i=1) or different according to the number "i" (i=2, 3, . . . );

"p$_i$" indicates a degree of saturation in % of a carrier molecule of general formula (I/a) by [Ex$_i$] enhancer molecules;

"(-)Cx" in "[(-)Cx$_j$]p$_2$" designates (-)Cx connecting molecules of anionic character of different ("x") kind linked to at least one carrier molecule of general formula (I/a) by covalent bonds;

"j" indicates whether the (-)Cx connecting molecules are identical (j=1) or different according to the number "j" (j=2, 3, . . . );

"p$_2$" indicates a degree of saturation in % of a carrier molecule of general formula (I/a) by [(-)Cx$_j$] connecting molecules of exclusively anionic character;

"Cx-Ex" in "[Cx$_{ck}$-Ex$_{ek}$]$_{p3}$" designates the Ex enhancer molecules of different ("x") kind linked to at least one carrier molecule of general formula (I/a) by covalent bonds indirectly through Cx connecting molecules of different ("x") kind linked to at least one carrier molecule of general formula (I/a);

"ck" indicates whether the Cx connecting molecules are identical (ck=1) or of different kind (ck=2, 3, . . . );

"ek" indicates whether the Ex enhancer molecules are identical (ek=1) or of different kind (ek=2, 3, . . . );

"p$_3$" indicates a degree of saturation in % of a carrier molecule of general formula (I/a) by [Ex$_{ek}$] enhancer molecules linked indirectly to Cx$_{ck}$ connecting molecules;

"p$_1$"+"p$_2$"+"p$_3$" is >0 and ≦100, and at least two of "p$_1$," "p$_2$" and "p$_3$" are greater than 0; and the Ex molecules in [Ex$_i$] and the (-)Cx molecules in [(-)Cx$_j$] are the same or different than the Ex and Cx molecules in [Cx$_{ck}$-Ex$_{ek}$].

4. A polycation bioconjugate, comprising:
one or more carrier molecules having free α-aiming groups, and one or more enhancer or connecting molecules, wherein the polycation bioconjugate has the general formula (I)

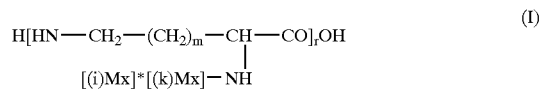

wherein
"r" is a mean value between 20 and 400 that designates the number of diaminomonocarbonic acyl group monomers;
"m"=0, 1, 2, 3, . . . ;
[(k)Mx] designates enhancer molecules and/or connecting molecules linked by covalent (=k) bonds to a carrier molecule;
[(i)Mx] designates enhancer molecules linked by ionic (=i) bonds to a carrier molecule, wherein the Mx functional groups may be the same or different, and the enhancer molecules can be linked directly and/or indirectly, through a connecting molecule, to the carrier molecule, and wherein when both [(k)Mx] and [(i)Mx] occur within the same polycation bioconjugate [(i)Mx]*[(k)Mx] is symbolized by [(k/i)Mx];

the carrier molecules are of the same configuration (either D- or L-), and the individual monomers are not linked together by their amino groups in the α-positions, and are linked together by amino groups in other positions according to the value of m, wherein the carrier molecules have a general formula (I/a):

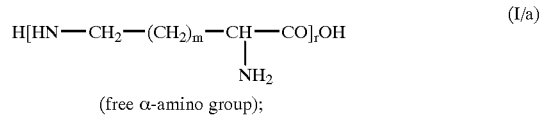

wherein [(i)Mx]=[(-)Ax$_s$]$_t$ and at least one carrier molecule is linked with one or more enhancer molecules [(-)Ax$_s$] of anionic character, wherein the Ax, molecules may be the same or different, wherein "Ax" in "[(-)Ax$_s$]$_t$" designates the (-)Ax enhancer molecules of anionic character of same or different ("x") kind linked to at least one carrier molecule of general formula (I/a) by ionic bonds;

"s" indicates whether the Ax enhancer molecules are identical (s=1) or of different kind (s=2, 3, . . . ); and "t" indicates a degree of saturation in % of a carrier molecule of general formula (I/a) by [(-)Ax$_s$] enhancer molecules, t having a value which is >0 and ≦100.

5. The polycation bioconjugate of claim 1, wherein [(k/i)Mx]=[(-)Cx$_j$]$_{p2}$*[(+)Kx$_u$]$_z$, wherein "(+)Kx" in "[(+)Kx$_u$]$_z$" designates the (+)Kx enhancer molecules of cationic character of same or different ("x") kind linked to at least one carrier molecule of general formula (I/a) by ionic bonds indirectly through the [(-)Cx$_j$]$_{p2}$ connecting molecules of anionic character;

"u" indicates whether the (+)Kx enhancer molecules are identical (u=1) or of different kind (u=2, 3, . . . ); and "z" indicates a degree of saturation in % of a carrier molecule of general formula (I/a) by [(+)Kx$_u$] enhancer molecules, z having a value which is >0 and ≦100.

6. The polycation bioconjugate of claim 5, wherein [(k/i)Mx]={[(-)Cx$_j$]$_{p2}$*[(+)Kx$_u$]$_z$}*[(-)Ax$_s$]$_t$, wherein "Ax" in "[(-)Ax$_s$]$_t$" designates the (-)Ax enhancer molecules of anionic character of same or different ("x")

kind linked to at least one carrier molecule of general formula (I/a) by ionic bonds;

"s" indicates whether the Ax enhancer molecules are identical (s=1) or of different kind (s=2, 3, . . . ); and "t" indicates a degree of saturation in % of a carrier molecule of general formula (I/a) by [(-)Ax$_s$] enhancer molecules, t having a value which is >0 and ≦100.

7. The polycation bioconjugate of claim 3, wherein [(k/i)Mx]=

$[Ex_i]_{p1}*[(-)Ax_s]_t$ or $[Cx_{ck}-Ex_{ek}]_{p3}*[(-)Ax_s]_t$ or $[Ex_i]_{p1}+[Cx_{ck}-Ex_{ek}]_{p3}*[(-)Ax_s]_t$, wherein "Ax" in "[(-)Ax$_s$]$_t$" designates the (-)Ax enhancer molecules of anionic character of same or different ("x") kind linked to at least one carrier molecule of general formula (I/a) by ionic bonds;

"s" indicates whether the Ax enhancer molecules are identical (s=1) or of different kind (s=2, 3, . . . );

"t" indicates a degree of saturation in % of a carrier molecule of general formula (I/a) by [(-)Ax$_s$] enhancer molecules; and "p$_1$"+"p$_3$"+"t" is >0 and ≦100, and at least one of "p$_1$" and "p$_3$" is greater than 0, and t is greater than zero.

8. The polycation bioconjugate of claim 3, wherein [(k/i)Mx]=

$[Ex_i]_{p1}+\{[(-)Cx_j]_{p2}*[(+)Kx_u]_z\}$ or $[Cx_{ck}-Ex_{ek}]_{p3}+\{[(-)Cx_j]_{p2}*[(+)Kx_u]_z\}$ or $[Ex_i]_{p1}+[Cx_{ck}-Ex_{ek}]_{p3}+\{[(-)Cx_j]_{p2}*[(+)Kx_u]_z\}$, wherein "(+)Kx" in "[(+)Kx$_u$]$_z$" designates the (+)Kx enhancer molecules of cationic character of same or different ("x") kind linked to at least one carrier molecule of general formula (I/a) by ionic bonds indirectly through the $[(-)Cx_j]_{p2}$ connecting molecules of anionic character, "u" indicates whether the (+)Kx enhancer molecules are identical (u=1) or of different kind (u=2, 3, . . . );

"z" indicates a degree of saturation in % of a carrier molecule of general formula (I/a) by [(+)Kx$_u$] enhancer molecules; and "p$_1$"+"p$_3$"+"z" is >0 and ≦100, and at least one of "p$_1$" and "p$_3$" is greater than 0, and z is greater than zero.

9. The polycation bioconjugate of claim 8, wherein [(k/i)Mx]=

$[Ex_i]_{p1}+\{[(-)Cx_j]_{p2}*[(+)Kx_u]_z*[(-)Ax_s]_t\}$ or $[Cx_{ck}-Ex_{ek}]_{p3}+\{[(-)Cx_j]_{p2}*[(+)Kx_u]_z*[(-)Ax_s]_t\}$ or $[Ex_i]_{p1}+[Cx_{ck}-Ex_{ek}]_{p3}+\{[(-)Cx_j]_{p2}*[(+)Kx_u]_z*[(-)Ax_s]_t\}$, wherein "Ax" in "[(-)Ax$_s$]$_t$" designates the (-)Ax enhancer molecules of anionic character of same or different ("x") kind linked to at least one carrier molecule of general formula (I/a) by ionic bonds;

"s" indicates whether the Ax enhancer molecules are identical (s=1) or of different kind (s=2, 3, . . . );

"t" indicates a degree of saturation in % of a carrier molecule of general formula (I/a) by [(-)Ax$_s$] enhancer molecules; and "p$_1$"+"p$_3$"+"t"+"z" is >0 and ≦100, and at least one of "p$_1$" and "p$_3$" is greater than 0, and t and z are each greater than zero.

10. A polycation bioconjugate, comprising:

one or more carrier molecules having free α-amino groups, and one or more enhancer or connecting molecules, wherein the polycation bioconjugate has the general formula (I)

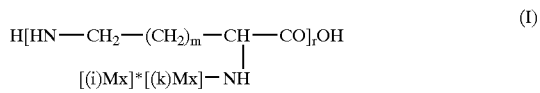

wherein

"r" is a mean value between 20 and 400 that designates the number of diaminomonocarbonic acyl group monomers;

"m"=0, 1, 2, 3, . . . ;

[(k)Mx] designates enhancer molecules and/or connecting molecules linked by covalent (=k) bonds to a carrier molecule;

[(i)Mx] designates enhancer molecules linked by ionic (=i) bonds to a carrier molecule, wherein the Mx functional groups may be the same or different, and the enhancer molecules can be linked directly and/or indirectly, through a connecting molecule, to the carrier molecule, and wherein when both [(k)Mx] and [(i)Mx] occur within the same polycation bioconjugate [(i)Mx] *[(k)Mx] is symbolized by [(k/i)Mx];

and a nucleic acid linked by an ionic bond to at least one carrier molecule.

11. The polycation bioconjugate of claim 1, wherein the bioconjugate comprises at least one enhancer molecule selected from the group consisting of an antiproliferative compound, an antimicrobial compound, an antiviral compound, a nucleic acid, a paramagnetic metal ion, a complex containing a paramagnetic metal ion, an immunomodulant compound, an antibody and fragments and derivatives thereof, a peptide and fragments and derivatives thereof, a protein and fragments and derivatives thereof, and a hormone and fragments and derivatives thereof.

12. The polycation bioconjugate of claim 3, wherein the bioconjugate comprises at least one enhancer molecule selected from the group consisting of an antiproliferative compound, an antimicrobial compound, an antiviral compound, a nucleic acid, a paramagnetic metal ion, a complex containing a paramagnetic metal ion, an immunomodulant compound, an antibody and fragments and derivatives thereof, a peptide and fragments and derivatives thereof, a protein and fragments and derivatives thereof, and a hormone and fragments and derivatives thereof.

13. The polycation bioconjugate of claim 4, wherein the bioconjugate comprises at least one enhancer molecule selected from the group consisting of an antiproliferative compound, an antimicrobial compound, an antiviral compound, a nucleic acid, a paramagnetic metal ion, a complex containing a paramagnetic metal ion, an immunomodulant compound, an antibody and fragments and derivatives thereof, a peptide and fragments and derivatives thereof, a protein and fragments and derivatives thereof, and a hormone and fragments and derivatives thereof.

14. The polycation bioconjugate of claim 11, wherein the enhancer molecule is a monoclonal antibody having an affinity to a surface antigen of a tumor cell.

15. The polycation bioconjugate of claim 11, wherein the enhancer molecule is a compound having an affinity to a receptor, wherein the receptor is present in a greater ratio on a surface of a tumor cell than on a surface of a non-tumor cell.

16. The polycation bioconjugate of claim 12, wherein the enhancer molecule is a monoclonal antibody having an affinity to a surface antigen of a tumor cell.

17. The polycation bioconjugate of claim 12, wherein the enhancer molecule is a compound having an affinity to a receptor, wherein the receptor is present in a greater ratio on a surface of a tumor cell than on a surface of a non-tumor cell.

18. The polycation bioconjugate of claim 13, wherein the enhancer molecule is a monoclonal antibody having an affinity to a surface antigen of a tumor cell.

19. The polycation bioconjugate of claim 13, wherein the enhancer molecule is a compound having an affinity to a receptor, wherein the receptor is present in a greater ratio on a surface of a tumor cell than on a surface of a non-tumor cell.

20. The polycation bioconjugate of claim 4, wherein Ax is a nucleic acid.

* * * * *